United States Patent [19]

Groll et al.

[11] Patent Number: 4,681,735

[45] Date of Patent: Jul. 21, 1987

[54] USE OF SILVER-FREE PALLADIUM ALLOYS FOR FIRING ON DENTAL CERAMICS

[75] Inventors: Werner Groll, Karlstein; Gernot Schöck, Bruchköbel; Doris Hathaway, Hanau; Rudolf Wagner, Remchingen, all of Fed. Rep. of Germany

[73] Assignee: Degussa Aktiengesellschaft, Frankfurt am Main, Fed. Rep. of Germany

[21] Appl. No.: 775,246

[22] Filed: Sep. 12, 1985

[30] Foreign Application Priority Data

Jun. 24, 1985 [DE] Fed. Rep. of Germany ....... 3522523

[51] Int. Cl.⁴ ................................................ C22C 5/04
[52] U.S. Cl. .................................................... 420/464
[58] Field of Search ................................. 470/463–465

[56] References Cited

U.S. PATENT DOCUMENTS

| | | | |
|---|---|---|---|
| 4,063,937 | 12/1977 | Goltsov et al. | 420/463 |
| 4,261,744 | 4/1981 | Boyajion | 420/463 |
| 4,400,350 | 8/1983 | Wagner | 420/464 |

FOREIGN PATENT DOCUMENTS

| | | |
|---|---|---|
| 3146794 | 6/1983 | Fed. Rep. of Germany . |
| 3244802 | 1/1984 | Fed. Rep. of Germany . |
| 3239338 | 2/1984 | Fed. Rep. of Germany ...... 420/464 |
| 3324987 | 6/1984 | Fed. Rep. of Germany . |
| 3247398 | 7/1984 | Fed. Rep. of Germany . |
| 3316595 | 11/1984 | Fed. Rep. of Germany . |

Primary Examiner—Christopher W. Brody
Attorney, Agent, or Firm—Cushman, Darby & Cushman

[57] ABSTRACT

Economical but readily workable palladium alloys for baking on dental ceramics consist of 60 to 80% palladium, 0 to 8% gold, 0 to 5% platinum, 0 to 1% ruthenium and/or rhenium, 2 to 20% copper, 1 to 12% tin and/or indium, 0.2 to 5% of at least one of the elements tungsten, molybdenum, niobium, and tantalum, and 0 to 15% cobalt, with the proviso that the sum of tin and indium must be between 5 and 14%.

6 Claims, No Drawings

USE OF SILVER-FREE PALLADIUM ALLOYS FOR FIRING ON DENTAL CERAMICS

BACKGROUND OF THE INVENTION

The invention is directed to the use of silver-free palladium alloys as materials for baking on dental ceramics.

The complex requirements which have to be fulfilled from fixed dental prosthesis work are the reason why crowns and bridges to a great extent are made from metal. Metallic dental prosthesis predominantly for esthetic reasons are veneered with dental ceramic so that the alloys must be compatible with the current types of dental ceramic. There have proven good for these uses high gold content alloys having about 60–90% gold, about 1–15% palladium, about 1–15% platinum, additionally silver, tin, indium and/or iron and grain refining elements such as iridium, ruthenium and/or rhenium. The high price of noble metals and the cost explosion in public health in recent years, however, have led to the development of alloys with a reduced gold content. Such alloys made of gold-palladium and gold-palladium-silver, however, always contain about 50–60% gold. Silver-containing alloys thereby frequently cause a green discoloration of the dental ceramic in the firing-on process and are seldom used in practice.

Therefore, in recent years there have been developed silver-free palladium based alloys which, because of the lower density and favorable price of palladium, represent the economical type of noble porcelain fused to metal alloy. A further price reduction is only possible by a reduction of the palladium content. Alloys based on palladium-cobalt (e.g. German OS No. 3324987 and Boyajian U.S. Pat. No. 4,261,744), especially in the range of lower palladium concentrations (about 75% and less), show bubble formation and discoloration in the veneering ceramic. The formation of bubbles may be suppressed by adding zinc, aluminium, or silicon, but these alloys then show solid state transformations which create problems in regard to the accuracy of fit of the dental prosthesis.

Furthermore, there are known numerous palladium-copper alloys with one or more of alloying elements tin, indium, cobalt, and grain refining additives of ruthenium and rhenium (e.g. German OS No. 3316595 and related Wagner U.S. application Ser. No. 607,701 filed May 7, 1984 and now allowed, German OS No. 3244802, German OS No. 3146794, German OS No. 3239338, and German OS No. 3247398). All of these alloys additionally contain gallium as an alloy component since this clearly improves the castability of the alloys. Without gallium, the casting results of these alloys can only be reproduced with difficulty, and frequently a formation of voids is observed. Gallium greatly lowers the solidus temperature and widens the melting range. Therefore the high-temperature-strength during baking of the ceramic is reduced, and there is an increased possibility of getting undesired segregations to be avoided upon solidification. Besides, gallium causes a strong increase in hardness. Gallium-containing alloys exhibit a heterogeneous structure and, therefore, are susceptible to corrosion. In addition an increased tendency to bubble formation in the ceramic veneer is observed particularly in alloys with low palladium concentrations.

The known palladium-copper based alloys usually reveal a coefficient of thermal expansion less than $14.0 \times 10^{-6}/K$ so that the compatibility with some new higher expanding dental ceramics no longer is guaranteed.

Therefore, it was the problem of the present invention to develop silver-free palladium alloys as materials for baking on dental ceramics which should be as cheap as possible, extra hard, and compatible with the known dental ceramics. Besides, they should be readily workable even without the addition of gallium and should reveal a solidus temperature exceeding 1150° C.

Unless otherwise indicated, all parts and percentages are by weight.

SUMMARY OF THE INVENTION

This problem was solved according to the invention by using an alloy consisting of 60 to 80% palladium, 0 to 8% gold, 0 to 5% platinum, 0 to 1% ruthenium and/or rhenium, 2 to 20% copper, 1 to 12% tin and/or indium, 0.2 to 5% of at least one of the elements tungsten, molybdenum, niobium, and tantalum, and 0 to 15% cobalt, with the proviso that the sum of tin and indium must be between 5 and 14%.

Preferably, there are used palladium alloys which contain 0.5 to 2.5% of one or more of the elements tungsten, molybdenum, niobium, and tantalum. There have proven especially good silver-free palladium alloys containing 65 to 75% palladium, 10 to 15% copper, 5 to 10% tin, 2 to 6% indium, 0.1 to 1% ruthenium and/or rhenium, and 0.5 to 2.5% tungsten, with the proviso that the sum of the content of tin and indium is between 10 and 13%.

In order to develop the cheapest possible palladium alloys, there must be found suitable base metals which do not change too greatly the technical properties and the workability of the palladium even if added using higher concentrations. Since nickel, because of its known health hazard should not be used in a dental alloy and iron, chromium, and manganese clearly impair the properties, only copper and cobalt are the main alloying elements available to form a complete series of solid solutions with palladium. The hardness does not exceed 130 HV5 upon adding up to 20% of copper or cobalt, the melting range is only reduced slightly. However, cobalt leads to a strong increase in the coefficient of thermal expansion and to an intensive, dark blue-gray oxide color. Therefore the cobalt content should not exceed 15 wt.%. The alloy scales at copper contents of more than 20%, the oxide adherence to the metal is reduced. Adding 1–12% tin and/or 1–12% indium in varying ratios, the palladium content can be reduced further and the technical properties corresponding to the requirements for an extra hard porcelain fused to metal alloy can be attained. However, especially at palladium concentrations below 75%, too high concentrations of tin and indium will result in the formation of tin and indium rich phases and will lead to a strong increase in hardness. Alloys having a high tin and indium content frequently are prone to hot tearing. These disadvantageous effects of tin and indium, however, can be avoided if the sum of the contents of tin and indium does not exceed 14%.

All of these alloys in the composition range 60–80% Pd, 2–20% Cu, 0–15% Co, 1–12% Sn, 1–12% in, however, show poor workability.

The casting results using high copper containing allys are difficult to reproduce since these alloys are very sensitive to small changes of the casting conditions. The sprue cone was always porous and arched outwardly, the cast objects in part contain voids. Bubbles as well as discolorations develop during the bake on of the body porcelain. The cobalt containing alloys exhibit a better casting behavior; but the formation of bubbles in the ceramic veneer was even more pronounced compared to the copper rich alloys. Presumably, during the melting, the alloys take up gases which are set free again during solidication or ceramic firing.

Surprisingly, it has now been found that above all tungsten using concentrations of 0.2-5 wt.%, eliminates the above-mentioned disadvantages in workability without negatively influencing the technical properties. The castings of the copper rich alloys are free of voids, the results are reproducible. Molybdenum, niobium, and tantalum act similarly to tungsten. Upon veneering the casting with dental ceramic, a formation of bubbles is observed no longer, the green discoloration of the casting investment as well as the dental ceramic is suppressed. The cobalt rich alloys also can be veneered without bubbles in the ceramic using a tungsten content of 0.2-5%. The adhesion between the tungsten containing alloys and the dental ceramic is very good. These alloys, because of their high coefficients of thermal expansion (greater than $14.0 \times 10^{-6}/K$) are compatible with all types of dental ceramics, even with those revealing very high values.

Employing these alloys is not only limited to the porcelain fused to metal technique for fixed dental prosthesis. The alloys likewise are outstandingly suitable for not veneered and for synthetic resin veneered dental prosthesis. A use in the etching bridge technique is likewise possible.

The following table shows the composition of several alloys according to the invention and their essential properties. Thereby, these alloys (7 to 11) were compared with already known alloys (1-6).

The entire disclosure of German priority application No. P 3522523.8 is hereby incorporated by reference.

| Alloy No. | Composition in the weight % | | | | | | | | | | | Melting Range [°C.] | Hardness (as cast) [HV5] | 0,2%-Yield strength [Nmm$^{-2}$] | Coefficient of thermal Expansion RT-600° C. $\times 10^{-6} K^{-1}$ | Casting Behavior | Veneering Properties |
|---|---|---|---|---|---|---|---|---|---|---|---|---|---|---|---|---|---|
| | Au | Pd | Ru | Co | Cu | Ga | In | Si | Sn | Ta | W | | | | | | |
| 1 | — | 69.5 | 0.5 | 19.5 | — | — | 5 | 0.2 | 5.3 | — | — | 1220-1180 (635-680° C.) (therm. effect) | 320 | — | 15.3 | good | bubbles |
| 2 | 2 | 78.5 | 0.4 | — | 10 | 9.1 | — | — | — | — | — | 1185-1065 | 405 | — | 13.6 | good | bubbles |
| 3 | — | 73.2 | 0.3 | — | 15 | 1.5 | 5 | — | 5 | — | — | 1270-1145 | 260 | — | 13.7 | good | bubbles |
| 4 | — | 69.5 | 0.5 | — | 13.5 | — | 9 | — | 7.5 | — | — | 1220-1170 | 315 | — | 14.6 | fracture of the castings | bubbles |
| 5 | — | 69.5 | 0.5 | — | 19.5 | — | 5 | — | 5.5 | — | — | 1225-1175 | 235 | 485 | 14.2 | sprue cones with bubbles in part voids | bubbles |
| 6 | — | 69.5 | 0.5 | 12 | 8 | — | 10 | — | — | — | — | 1230-1170 | 290 | — | 15.5 | good | bubbles |
| 7 | 6 | 63.5 | 0.5 | 2 | 14.5 | — | 5 | — | 7 | — | 1.5 | 1240-1160 | 295 | — | 14.4 | good | good |
| 8 | — | 72 | 0.5 | 2 | 12.5 | — | 5 | — | 7 | — | 1 | 1285-1200 | 230 | 515 | 14.2 | good | good |
| 9 | — | 72 | 0.5 | 2 | 13.5 | — | 3 | — | 8 | — | 1 | 1285-1190 | 230 | 500 | 14.4 | good | good |
| 10 | — | 74 | 0.8 | — | 12.2 | — | 3 | — | 9 | 1 | — | 1285-1185 | 235 | 495 | 14.4 | good | good |
| 11 | — | 77.5 | 0.5 | 7 | 3 | — | 10 | — | 1 | — | 1 | 1320-1240 | 260 | — | 14.4 | good | good |

What is claimed is:

1. A silver-free palladium alloy suitable as a material for baking on a dental ceramic consisting of 60 to 80% palladium, 0 to 8% gold, 0 to 5% platinum, 0 to 1% of ruthenium, rhenium, or of both ruthenium and rhenium, 2 to 20% copper, 1 to 12% of tin, indium, or of both tin and indium, 0.2 to 5% of at least one of the elements tungsten, molybdenum, niobium, and tantalum, and 0 to 15% cobalt, with the proviso that the sum of tin and indium must be between 5 and 14%.

2. A silver-free alloy according to claim 1 containing 0.2 to 5% of tungsten.

3. A silver-free alloy according to claim 1 containing 0.5 to 2.5% of at least one of the elements tungsten, molybdenum, niobium, and tantalum.

4. A silver-free alloy according to claim 1 free of cobalt.

5. A silver-free alloy according to claim 1 containing cobalt.

6. A silver-free alloy according to claim 1 consisting of 65 to 75% palladium, 10 to 15% copper, 5 to 10% tin, 2 to 6% indium, 0.1 to 1% of ruthenium, rhenium, or a mixture of ruthenium and rhenium and 0.5 to 2.5% tungsten, with the proviso that the sum of the contents of tin and indium is between 10 and 13%.

* * * * *